United States Patent [19]
Carroll et al.

[11] Patent Number: 4,774,094
[45] Date of Patent: Sep. 27, 1988

[54] STABILIZED APM IN COMESTIBLES

[75] Inventors: Thomas J. Carroll, Oak Ridge, N.J.; Gary S. Kehoe, Ridgefield, Conn.

[73] Assignee: Nabisco Brands, Inc., Parsippany, N.J.

[21] Appl. No.: 840,299

[22] Filed: Mar. 14, 1986

Related U.S. Application Data

[63] Continuation-in-part of Ser. No. 717,630, Mar. 29, 1985, abandoned.

[51] Int. Cl.[4] ............................................. A23G 3/30
[52] U.S. Cl. ........................................ 426/3; 426/654; 426/658; 424/48
[58] Field of Search ....................................... 426/3–6, 426/654, 658; 424/48

Primary Examiner—Jeanette Hunter
Attorney, Agent, or Firm—Richard Kornutik

[57] ABSTRACT

L-aspartic acid sweetening agent derivatives are stabilized in comestibles containing ≥2% moisture by being formulated with cooked aqueous hydrogenated starch hydrolysate having a moisture content of 10±6%. Optionally, glycerine may also be used.

25 Claims, No Drawings

STABILIZED APM IN COMESTIBLES

CROSS REFERENCE TO RELATED PATENT APPLICATIONS

This patent application is a continuation-in-part of U.S. patent application Ser. No. 717,630 filed Mar. 29, 1985 now abandoned and entitled "Stabilized APM in Comestibles".

BACKGROUND OF THE INVENTION

1. Field of the Invention

The present invention relates to comestibles such as chewing gum containing ≧2% moisture and made with L-aspartyl-L-phenylalanine methyl ester (APM or aspartame) in which the aspartame has been significantly stabilized against decomposition, during its shelf life, into decomposition products such as diketopiperazine, by being formulated with aqueous hydrogenated starch hydrolystate that has been cooked to achieve a moisture content of about 10±6%. Glycerine may also be added with the cooked hydrogenated starch hydrolysate.

2. Description of the Prior Art

Aspartame which is used extensively in many types of sugarless foodstuffs, or other comestible products, such as chewing gum, is known to readily decompose in the presence of moisture into decomposition products such as diketopiperazine which causes a significant loss in the sweetness properties of such products during their shelf lives. Many attempts have been made by those producing the various types of products in which aspartame is used in order to provide means for stabilizing the aspartame against such decomposition processes. Such means have included encapsulating the aspartame in various film forming materials (U.S. Pat. Nos. 3,929,988, 4,384,004 and International Patent Application WO No. 84/0320), or by saturating an aqueous dispersing agent used in the product with the aspartame (EPA 102,032), or by formulating the product with stabilizing agents for the aspartame such as commercially available aqueous hydrogenated starch hydrolysate which has a moisture content of about 20 to 35%. (see in this regard U.S. patent applications Ser. No. 677,717 filed Dec. 4, 1984 in the names of D. R. Friello, et al, and entitled "Comestible Containing Moisture and Shelf Storage Stabilized L-Aspartic Acid Derivative", and refiled as Ser. No. 865,493 on May 20, 1983 and Ser. No. 677,716 filed Dec. 4, 1984 in the names of D. R. Friello et al. and entitled "Comestible Containing Moisture, CaCO3 and Shelf Storage Stabilized L-Aspartic Acid Derivative", and refiled as Ser. No. 867,821, on May 27, 1986."

Each of such various prior art means, however, have certain drawbacks. The encapsulation means requires a separate, time-consuming and relatively expensive procedure for encapsulating the aspartame which amounts to a separate processing operation.

Saturating the moisture content of a product with aspartame requires the use of excess amounts of the aspartame needed to achieve a certain level of sweetness. Since aspartame is a relatively expensive material, this proposed solution to the aspartame decomposition procedure is a rather expensive one. Further, it does not prevent the decomposition of the aspartame into undesired decomposition products such as diketopiperazine.

Although the use of aqueous hydrogenated starch hydrolysate having a moisture content of 20 to 35% as an aspartame stabilizer, as taught in said U.S. Ser. Nos. 677,716, 677,717, 867,821 and 865,493 does provide a fair degree of long term aspartame stability in chewing gum, a significant degree of improvement in such stabilizing action is still desired for commercial reasons, i.e., because of the relatively high cost of the aspartame, and to extend the shelf life of the products made with aspartame.

It is also desired to use aspartame in products having relatively high moisture contents in order to avoid the need for stringent anhydrous operating conditions that are required when producing chewing gum products having very low moisture contents, i.e., less than 1 to 2%. See in this regard European Patent Application 82670 and International Patent Application WO No. 84-10693.

Further, various of these prior art chewing gum products which have such very low moisture contents, i.e., of about 1 to 2%, also have relatively low equilibrium relative humidity (ERH) values, i.e., of the order to about 10 to 25. During the storage of such products under ambient conditions of about 40 to 70% relative humidity and about 20° to 30° C., the (low value) ERH properties of such products will cause such products to absorb relatively large amounts of water from the atmosphere.

Such increased amounts of water will lead to a more accelerated rate of decomposition of any unprotected APM therein; and will adversely affect other qualities of the products.

Thus, such products having very low ERH values would require that they be processed amd wrapped under special atmospheric conditions of low humidity and controlled temperature. Such conditions are expensive and difficult to maintain.

Equilibrium relative humidity (ERH) or relative vapor pressure is the humidity at which a foodstuff neither gains nor loses moisture and the figure is expressed as a percentage. A discussion of ERH relative to food products and a method for the determination thereof is to be found in "Chocolate, Cocoa and Confectionery," Science and Technology, Second Edition, 1980, Bernard W. Minifie, AVI Publishing Co., Inc. Westport, Conn., U.S.A., Appendix I, pp. 672-677 (the disclosure of which is incorporated herein by reference). The test procedure disclosed in such publication is the one used for testing and evaluating the compositions disclosed herein.

U.S. Pat. No. 4,248,895 discloses the preparation of a dried non-hygroscopic free flowing powder that is made by drying a higher polyalcohol, such as hydrogenated starch hydrolysate, with a concentrated protein extract. The dried material has a moisture content of about 2-6% and may be used as a sweetener in confections such as chewing gum to provide products having prolonged shelf life in terms of retained flexibility and softeners. Other non-sugar sweeteners may be used with the dried, powdered, higher alcohol sweetener such as L-aspartyl-L-phenylalanine. The dried hydrogenated starch hydrolysate may also be used in combination with hydrogenated starch hydrolysate syrup having a moisture content of 15 to 40%.

U.S. Pat. No. 4,382,962 discloses the preparation of sugarless chewing gum made with a specific hydrogenated starch hydrolysate composition that is designed to replace all or a portion of the mannitol previously used with xylitol and/or sorbitol in such products. Cyclamates and the salts of saccharin may be also used in such products when the product contains a liquid filler (column 4, lines 20–45).

Cooked hydrogenated starch hydrolysate which has a moisture content of about 8±4% has also been proposed for use in flexible sugarless chewing gum. See in this regard U.S. patent application Ser. No. 717,765 filed Mar. 29, 1985 in the names of Thomas J. Carroll et al. and entitled "Flexible Sugarless Chewing Gum", and the continuation-in-part of said U.S. Ser. No. 717,765 filed Mar. 14, 1986 as Ser. No. 840,300.

Therefore, it has not been readily possible, heretofore, to economically provide a means for stabilizing aspartame in chewing gum products having a relatively high moisture content so as to provide for more optimum stabilization effects.

An object of the present invention is to provide comestibles such as chewing gum products containing $\geq 2\%$ moisture and sweetened, at least in part, by aspartame, and wherein relatively high levels of aspartame stability are achieved during long term storage of the products.

A further object of the present invention is to provide such comestibles as have a relatively high ERH value.

SUMMARY OF THE PRESENT INVENTION

It has now been found, according to the present invention, that chewing gum products made with relatively large amounts of moisture, and sweetened, at least in part, with aspartame, can have such aspartame stabilized to a relatively high degree against decomposition into decomposition products such as diketopiperazine, by formulating the product with stabilizing amounts of aqueous hydrogenated starch hydrolysate having a cooked moisture content of about 10±6%.

DESCRIPTION OF THE PREFERRED EMBODIMENT

The cooked aqueous hydrogenated starch hydrolysate used in the compositions of the present invention as a stabilizer for the aspartame has a moisture content of about 10±6%, and preferably of about 10±4%. This cooked hydrogenated starch hydrolysate is prepared by cooking, or heating, commercially available aqueous solutions of the hydrogenated starch hydrolysate, which have moisture contents of about 20 to 35%, at a temperature of about 250° to 310° F., and preferably of about 260° to 290° F., until the desired low moisture content of the cooked material is attained. This may take about 0.5 to 1.0 hours for a 100 gallon batch of a commercially available aqueous solution of hydrogenated starch hydrolysate having a moisture content of about 25%.

The uncooked commercially available hydrogenated starch hydrolysate which may be used to form the cooked hydrogenated starch hydrolysate used in the compositions of the present invention may be a hydrogenated corn syrup or hydrogenated starch hydrolysate of varying dextrose equivalents (DE), such as are disclosed in U.S. Pat. Re. No. 26,959 and U.S. Pat. Nos. 3,556,811, 4,279,931 and 4,382,962, as well as various hydrogenated glucose syrups and/or reconstituted powders which contain sorbitol, hydrogenated disaccharides, tri- to hexa-hydrogenated saccharides, and hydrogenated higher polysaccharides, or mixtures of any two or more of the above.

The uncooked commercially available hydrogenated glucose syrups or hydrogenated starch hydrolysates and/or powders thereof may be produced by catalytic hydrogenation of standard glucose syrups (acid and/or enzyme converted) to the point where all the glucose end groups of the saccharides are reduced to alcohols, that is, dextrose to sorbitol. In the case of hydrogenated glucose syrups, the total solids contents will usually range from about 65 to about 80%, which solids are made of from about 4 to 70%, and preferably from about 4 to about 20%, sorbitol, from about 8 to about 65%, and preferably from about 20 to about 65%, hydrogenated disaccharides (that is, mannitol), and 20 to 80% of the higher ($\geq$ tri to hepta) hydrogenated saccharides. The preferred of the uncooked commercially available hydrogenated starch hydrolysates contain from about 8 to about 45%, and preferably about 15 to 45%, tri- to hepta-hydrogenated saccharides, and from about 10 to about 35%, and preferably about 15 to 25%, hydrogenated saccharides higher than hepta.

The commercially available hydrogenated starch hydrolysate is also referred to in the literature as hydrogenated glucose syrup, or by the trademark or tradename Lycasin polyol or Lonza polyol. The term hydrogenated starch hydrolysate will be used herein to designate such material. The hydrogenated starch hydrolysate is usually sold commercially in the form of an aqueous solution thereof having a moisture content of about 20 to 35%.

The chewing gum compositions of the present invention are made with about 20±10%, and preferably, about 15±5%, of the cooked hydrogenated starch hydrolysate. When less than about 10% of the cooked hydrogenated starch hydrolysate is used the resulting products have poor flexibility properties, and when more than about 30% of the cooked hydrogenated starch hydrolysate is used, the resulting product is too soft.

The chewing gum products of the present invention, have a moisture content of about 2 to 8%, and preferably of about 2 to 5%.

The chewing gum products of the present invention may also comprise about $\geq 0$ to 12%, and preferably about 5 to 9%, glycerine.

The glycerine assists in providing long term storage flexibility, and initial softness of chew. The glycerine may be cooked with the hydrogenated starch hydrolysate and added, as such, to the chewing gum formulation, or it may be added separately. When the glycerine is cooked with the hydrogenated starch hydrolysate, the cooking temperature should not exceed the decomposition temperature of the glycerine, which is about 290° C.

The chewing gum products of the present invention have ERH values of about $\geq 25$ to 50, and preferably of about 30 to 50, and most preferably about 30 to 40.

The cooked hydrogenated starch hydrolysate and/or the glycerine may be added to the gum base portion, or with the non-gum base components, when formulating the products of the present invention. The cooked hydrogenated starch hydrolysate, with or without glycerine cooked therewith, is cooled to below 150° F. before being admixed with the other components of the chewing gum products of the present invention.

When the cooked hydrogenated starch hydrolysate is prepared (cooked) with less than about 4% glycerine, the resulting product is in a glossy solid state at room temperature. When the cooked hydrogenated starch hydrolysate is made with about 4 to 12% glycerine, the resulting product is liquid or is pourable at room temperature.

This solid glossy material melts, or becomes pourable, at a temperature of about 212° to 220° F. When using cooked hydrogenated starch hydrolysate in the chewing gum products of the present invention which has been made with less than about 4% glycerine, it is preferable, to facilitate the incorporation of the cooked material into the chewing gum composition, to use the cooked hydrogenated starch hydrolysate just after it has been cooked, and it is still in a heated and liquid state. It is preferable under such circumstances to allow the cooked hydrogenated starch hydrolysate (made with less than 4% glycerine) to cool down to about 150° to 160° F. before incorporating it into the chewing gum formulation.

When the cooked hydrogenated starch hydrolysate is made with about 4 to 12% glycerin, it is preferable to cool it down to about 100° to 110° F. before it is added to the chewing gum formulation.

The preferred L-aspartic acid derivative to be used in the compositions of the present invention is, as noted above, L-aspartyl-L-phenylalanine methyl ester, known as aspartame. Other L-aspartic acid sweetening derivatives may also be used. Such derivatives are disclosed in U.S. Pat. No. 3,955,000 at column 3, line 63 to column 4, line 35, the disclosure of which is incorporated herein by reference. The following description will be directed to aspartame with the understanding that the other L-aspartic acid sweetening derivatives may also be used in lieu of and/or in addition to the aspartame. These compounds are also known as dipeptides.

The compositions of the present invention contain about 0.01 to 2.0, and preferably about 0.1 to 0.25%, of the aspartame.

The chewing gum products of the present invention do not contain a liquid filling, they are completely solid materials.

When made in stick form, the chewing gum products of the present invention are flexible. When prepared in stick form the sticks are about 0.065 to 0.072 inch in thickness, about ¾ inch in width and about 2 ⅜ to 3 inches in length.

The flexibility of the stick products of the present invention and those of the prior art products can be evaluated by the following test procedure:

A single stick of gum, which is at room temperature, i.e., 20°–25° C., is held between the thumb and index finger of both hands, along the wide sides of the stick, and within 0.5 to 1.0 inch of each end of the stick, and is then slowly twisted in opposite directions relative to the long axis of the wide side of the stick. A stick of gum made according to the present invention, which has good flexible properties, will bend or shape, without breaking or crumbling, after at least two or three 180° turns of the fingers, into a helical shaped structure before tearing.

A non-flexible stick of gum, on the other hand will typically break up or crumble after, or before, the completion, of only one 180° turn of the fingers.

The flexibility properties of stick chewing gum products made according to the present invention will last during prolonged storage of such products, i.e., for at least 9 to 12 months, when the products are stored at 40 to 70% relative humidity and at 20° to 30° C.

Although many prior art sugarless stick regular chewing gum products may pass the above described flexibility test when they are freshly made, and are warm, they will not do so after they have cooled down to room temperature i.e., 20°–25° C.

CHEWING GUM COMPOSITIONS

The chewing gum compositions contemplated by the present invention comprise all types of sugarless chewing gums and chewing gum formulations known to those skilled in the art, including the regular gum and the bubble gum types. Typical chewing gum compositions comprise a chewing gum base, a modifier, a bulking agent or sweetener, and one or more other additives such as flavoring agents, colorants and antioxidants. The modifying agents are used to soften, plasticize and/or compatibilize one or more of the components of the gum base and/or of the formulation as a whole.

The chewing gum products of the present invention would have the following formulation:

| Component | Weight Percent of Component | |
|---|---|---|
| | Broad Range | Preferred Range |
| gum base | 15 to 35 | 20 to 30 |
| cooked hydrogenated starch hydrolysate | 10 to 30 | 10 to 20 |
| glycerin | 0 to 12 | 5 to 9 |
| modifying agent other than glycerin | 0 to 5 | 0.3 to 3.0 |
| aspartame | 0.01 to 2 | 0.1 to 0.25 |
| non-nutritive sweetener (other than aspartame) | 0 to 2 | 0.1 to 0.4 |
| bulking agent or bulk sweetener | 20 to 70 | 30 to 50 |
| coloring agent | 0.1 to 0.5 | 0.15 to 0.3 |
| flavoring agent (other than sweetener) | 0.5 to 2.5 | 0.18 to 1.2 |
| moisture* | 2 to 8 | 2.0 to 5.0 |
| Total | 100 | 100 |

*Moisture content contributed by all components.

Gum Base

The composition of the gum base will vary depending on whether the gum base is to be used in a chewing gum product which is to be a regular, or non-bubble, gum product or a bubble gum product. For use in making a bubble gum or regular chewing gum product, the following gum base formulations may be used, in accordance with the present invention:

| | Weight percent of component in Gum base for | | | |
|---|---|---|---|---|
| | Bubble Gum Product | | Regular Gum Product | |
| Component | Broad Range | Preferred Range | Broad Range | Preferred Range |
| Masticatory material | 8–22 | 9–18 | 8–25 | 9–18 |
| plasticizer for masticatory material | 5–35 | 10–20 | 2–30 | 8–20 |
| hydrophilic detackifier | 0–30 | 4–10 | 5–35 | 10–25 |
| plasticizer for hydrophilic detackifier | 0–14 | 0–8 | 1–15 | 3–12 |
| wax | 3–15 | 5–10 | 4–20 | 8–15 |
| mineral filler | 1–35 | 10–22 | 5–35 | 15–30 |
| antioxidant | 0–0.1 | 0.05–0.09 | 0–0.1 | 0.03–0.09 |
| Total | 100 | | 100 | |

The masticatory substances are elastomeric materials which may be synthetic or natural in origin. The masticatory substances of synthetic origin would include styrene-butadiene copolymer, butyl rubber (which is isobutylene-isoprene copolymer) and polyisobutlyene. The natural masticatory substances would include chicle, crown gum, nispero, balata, jelutong, pendare, perillo, niger gutta, tunu, leche caspi, sorva and gutta hank kang.

The plasticizer for the masticatory substances will preferably comprise a hydrogenated ester gum, that is, a glycerol ester of hydrogenated rosin and/or dimerized ester gum. However, other resins may be employed such as pentaerythritol ester gum, polymerized ester gum, polyterpene resin and ester gum.

The hydrophilic-type detackifier is a material which will absorb saliva and would include vinyl polymers having a molecular weight of at least 2,000, and preferably of about 2,000 to 80,000 or more, such as polyvinyl acetate, polyvinyl butyl ether and copolymers of vinyl esters and/or vinyl ethers with ethylene.

The plasticizers for the hydrophilic type detackifiers would include one or more of triacetin, acetylated glycerides and other flavor adjuvants such as ethyl acetate and triethyl citrate, and others as listed in U.S. Pat. No. 4,452,820 at column 4, lines 27 to 46, the disclosure of which is incorporated herein by reference.

The oleaginous material includes waxes which are used primarily as compatibilizers/plasticizers between the elastomeric and resin phases, where such two phases are employed. Examples of the waxes are petroleum waxes such as paraffin wax and microcyrstalline wax; the polyethylene waxes; and natural waxes derived from eiter plant or animal sources such as candelilla wax, carnuba wax and bees wax. The oleaginous material may also include hydrogenated vegetable or animal fats, cocoa butter or other softening-emulsifying agents such as phosphatides such as lecithin and di- and triglycerides of fatty acids.

The mineral fillers would include calcium carbonate, titanium dioxide, talc, alumina, tricalcium phosphate and mixtures thereof. The compositions of the present invention can be formulated with materials such as calcium carbonate without having a deleterious effect on the stability of the aspartame.

In addition, the gum base may include antioxidants such as butylated hydroxy toluene, butylated hydroxy anisole and propyl gallate.

If desired, the aspartame may be employed together with another non-nutritive or artificial or intense sweetener such as poorly water-soluble, as well as water-soluble sweeteners such as the free acid form of saccharin, sodium, calcium or ammonium saccharin salts, dihydrochalcones, glycyrrhizin, dipotassium glycyrrhizin, glycyrrhizic acid/ammonium salt, talin, acesulfame K, as well as *Stevia rebaudiana* (Stevioside), *Richardell ducifica* (Miracle Berry), *Dioscoreophylim cumminisu* (Serendipity Berry), free cyclamic acid and cyclamate salts, and the like, or mixtures of any two or more of the above.

The artificial sweetener may be employed with non-sugar bulk sweeteners (other than the cooked hydrogenated starch hydrolysate) such as dry crystalline sugar alcohols such as sorbitol, xylitol and mannitol. The preferred products of the present invention are made without sugar or other utritive sweeteners.

In addition to the above, the chewing gum made by this invention can also contain conventional FD&C and natural coloring agents.

The flavoring which can be included in the chewing gum compositions made according to this invention can comprise one or more natural and/or synthetic flavors and/or oils derived from plants, leaves, flowers and fruit. Representative flavors and oils of these types include acids such as adipic, succinic and fumaric acid; citrus oils such as lemon oil, orange oil, lime oil and grapefruit oil; fruit essences, such as apple essence, pear essence, peach essence, strawberry essence, apricot essence, raspberry essence, cherry essence, plum essence and pineapple essence; essential oils such as peppermint oil, spearmint oil, mixtures of peppermint oil and spearmint oil, clove oil, bay oil, anise oil, oil of nutmeg, oil of sage, oil of bitter almonds, cassia oil and methylsalicylate (oil of wintergreen). Various synthetic flavors, such as those for a mixed fruit, may also be incorporated in the chewing gum with or without conventional preservatives.

GENERAL PREPARATION OF CHEWING GUM PRODUCT

The chewing gum products of the present invention are prepared by first separately preparing the gum base. To then prepare the sugarless chewing gum formulation, the gum base for the product is melted, at a temperature about 190° to 250° F., and the other components of the composition are added thereto. The resulting composition is uniformly admixed. Each of the components is usually separately added to the formulated composition and uniformly mixed in before the next component is added. All of the admixing operations are conducted at temperatures in the range of about 115° to 185° C., and preferably of about 115° to 130° C., for a total mixing time, at such temperatures, of about 10 to 20 minutes. These operations do not have to be conducted under anhydrous conditions in preparing the compositions of the present invention, and any amounts of moisture that are normally present in the raw materials, other than the uncooked hydrogenated starch hydrolysate, that are used in the compositions of the present invention do not usually have to be removed therefrom either prior to, or during, the formulating process. The one exception to this concept of not removing water occurs when using rubber latices as the source of the masticatory substance. As in prior art practice, the moisture content of the latex is, essentially, normally removed after coagulating the latex.

The chewing gum formulations disclosed herein may thus be prepared, and processed into chewing gum products, using conventional chewing gum formulation mixing, processing and packaging equipment and concepts.

The following examples are merely illustrative of the present invention and are not intended as a limitation upon the scope thereof.

PREPARATION OF CHEWING GUM COMPOSITIONS

Various chewing gum compositions were prepared using various of the gum bases prepared as described above. In preparing the chewing gum compositions, they were prepared in pilot plant sized batches in paddle mixers. In preparing each batch, the previously prepared gum base is melted at a temperature of up to about 245°±5° F. and is premixed with lecithin and color additive, and, optionally, the cooked hydrogenated starch hydrolysate, and glycerine, if the latter is used, until the temperature drops to about 185° to 189° F. Then there is sequentially added powdered sorbitol (at a temperature of $\leq 180°$ F.), liquid flavor (i.e., peppermint), liquid sorbitol, if used, glycerin, if used, alone or with the cooked hydrogenated starch hydrolysate, if the latter is not premixed with the gum base, any additional flavorants, and finally the aspartame, and, optionally, any other intense sweeteners. Each component is paddle mixed in before the next is added. Each mixing step takes about 0.5 to 5.0 minutes and the total mixing time is about 10-20 minutes. The resulting product is recovered and further processed and packaged using conventional chewing gum making procedures.

The cooked hydrogenated starch hydrolysate used in the chewing gum compositions evaluated in the Examples had a moisture content of 7.5% or 11.5% and was prepared by cooking, at 250° to 310° F., a commercially available aqueous hydrogenated starch hydrolysate whch had a solids content of 75±1%, a monosaccharide content of about 6 to 8%, a disaccharide content of about 50 to 55%, and a higher saccharide content of about 38 to 48%. The higher saccharides were about 20 to 25% in the 3–7 DP (degree of polymerization) range, and about 18 to 23% in the >7 DP range.

Unless otherwise indicated, the total water content reported below for each of the chewing gum formulations of the Examples is a calculated amount based on the water content of the cooked hydrogenated starch hydrolysate (HSH), about 10±6%, and glycerine, about 1 to 4%, (where used) plus any added water used in the respective formulations. The actual water content of these formulations is about 0.2 to 0.5% higher than the reported calculated values, since such additional amounts of water enter the final formulated product from the other components of the formulation and from the ambient atmosphere. The total of the reported weight percents for the respective formulations of these Examples will thus total about 100% plus the respectively reported calculated water contents.

The test formulations were prepared using batch pilot plant procedures. Prior to beginning the pilot plant batch making process, a batch of cooked HSH/glycerine was prepared, and then split into two half batches each of which contains one-half of each of the formulated amounts of the glycerine and the cooked hydrogenated starch hydrolysate that are to be used in making the product of each example. One of such premixtures is then used in each of steps 3 and 6 noted below.

STEP-WISE PILOT PLANT PROCEDURE

1. Into a pre-warmed sigma bladed mixer add molten gum base. The gum base temperature should be between 150°-200° F., and preferably between 170°-190° F.
2. With the blades of the mixer operating, and the temperature in the cited range, the lecithin is added and the mixing is continued for one minute.
3. Add one half of the cooked HSH/glycerine premixture, or the first ½ of the HSH, and mix for two minutes, or until homogeneous.
4. Add ½ of the sorbitol powder and continue mixing for two minutes.
5. The liquid flavor is then added and mixing is continued for one minute.
6. Add the second half of the cooked HSH/glycerine premixture, or the second ½ of the cooked HSH, and mix for two minutes.
7. Add the remaining sorbitol powder and the non-nutritive sweetener. Prior to production of the batch, the non-nutritive sweetener is premixed with a small portion of the sorbitol powder. Continue mixing for two minutes, or until the batch is homogeneous. The final gum temperature is approximately 112° F.
8. The gum is removed from the mixer and conditioned at 70° F./42-55% R.H. prior to forming.
9. The gum is rolled and scored into a stick configuration. Mannitol is applied to the surface of the scored gum to prevent surface adhesion. The gum is then packaged in fin-seal foil pouches and sealed.

EXAMPLES 1 and 2

Using the pilot plant procedure described above two (2) chewing gum products were prepared from the following formulations, in % by weight.

| Component | Weight % of Compound Example | |
|---|---|---|
| | 1 | 2 |
| styrene-butadiene copolymer based gum base | 30 | 30 |
| sorbitol, powder | 43 | 40 |
| cooked hydrogenated starch hydrolysate | 20 | 20 |
| glycerine | 5 | 8 |
| flavor | 1 | 1 |
| lecithin | 1 | 1 |
| aspartame | 0.2 | 0.2 |
| moisture | Ca. 3 | Ca. 2.2 |
| | 100 | 100 |

Ca. = about

The cooked hydrogenated starch hydrolysate used in Example 1 and 2 had a moisture content of, respectively, 11.5 and 7.5%.

The chewing gum products of the present invention were flexible, in stick form. When tested for flexibility, as described above, individual sticks of gum made from each of the Example 1 and 2 products were twisted 3 times before breaking. These tests for flexibility were conducted, periodically, over a storage period of up to about 55 days under accelerated aging conditions of 100°-105° F. and about 30% relative humidity.

The packaged chewing gum products of the present invention made in Examples 1 and 2 were also evaluated for the shelf life stability of the aspartame used therein while stored for up to about 40 to 55 days under accelerated aging conditions at 100°-105° F. and ambiant, about 30°, relative humidity with the following results:

TABLE 1

| % APM Recovery During Accelerated Aging Storage of Example 1 and 2 Chewing Gum Samples | | | | | | |
|---|---|---|---|---|---|---|
| % APM Recovery | Days Storage | | | | | |
| | 0 | 14 | 21 | 28 | 35 | 41 | 56 |
| Example 1 | 93 | NT | 86.5 | — | — | 79.5 | — |
| Example 2 | 96 | 94.5 | NT | 81.5 | 80 | — | 74 |

NT = not tested at this time interval

The APM was analyzed for, employing standard gas chromatography procedures, first at zero time, i.e., within 48 hours after the product was first made and prior to its being subjected to any accelerated aging, and then at various intervals, as noted in Table 1 above, after 14 to 56 days of accelerated aging time. Based on experience, each day of accelerated aging time is equivalent to about 7 to 7.5 days of commercial storage aging time. Thus 40 days of accelerated aging time is equivalent to about 280 to 300 days, or about 10 months, of commerical storage time, and 50 days of accelerated aging time is equivalent to about 350 to 375 days, or at least one year, of commercial storage time. These test results thus indicate that the aspartame is very stable in the compositions of the present invention in that at least 80% of the APM is retained and is recoverable for at least 40 days of accelerated aging and at least 70% of the aspartame is retained and is recoverable for at least 50 days of accelerated aging time.

EXAMPLES 3 to 8

A series of six sugarless stick chewing gum products were evaluated for ERH values and flexibility values. The compositions of these products are indicated below, or in Table 2.

Products 3 and 4 were made according to the present invention, as described above, using either a styrene-butadiene based gum base (Gum Base A) or a gum base made from an admixture of styrene-butadiene elastomer and polyisobutylene elastomer (Gum Base B). Products 5 and 6 were made with Gum Base A and were based on prior art composition technology (high glycerine, low moisture content). Products 5 and 6 were otherwise prepared as described above. Product 7 is an off-the-shelf sample of Trident spearmint gum manufactured by Warner Lambert Co. Product 8 was an off-the-shelf sample of Extra bubble gum manufactured by Wm. Wrigley Jr. Company. (Trident and Extra are trademarks of such companies).

The list of contents of the Extra product, as indicated on the label thereof, is sorbitol, gum base, mannitol, glycerol, artificial and natural flavors, lecithin, aspartame, artificial colors and butylated hydroxy toluene.

The list of contents of the Trident product, as indicated on the label thereof, is sorbitol, gum base, glycerine, mannitol, softeners, natural and artificial flavors, and sodium saccharin.

The compositions of the Trident and Extra products thus do not contain hydrogenated starch hydrolysate in any form.

It is believed that the Trident product contains about 2% water and that the Extra product contains about 1% water. The exact formulated contents of these products is not known.

The products were each analyzed for their ERH value, as described above. The ERH values of these products are shown below in Table 2.

TABLE 2

| Component | Example 3-8 Formulations | | | | | |
|---|---|---|---|---|---|---|
| | 3 | 4 | 5 | 6 | 7 | 8 |
| Gum base | 27.0 | 27.0 | 30.0 | 30.0 | — | — |
| sorbitol powder | 47.4 | 46.3 | 60.0 | 50.0 | — | — |
| cooked HSH | 15.0 | 16.5 | 0 | 0 | — | — |
| glycerine | 8.0 | 8.0 | 8.0 | 18.0 | — | — |
| peppermint oil | 1.2 | 1.2 | 1.0 | 1.0 | — | — |
| lecithin | 1.2 | 0.7 | 1.0 | 1.0 | — | — |
| aspartame | 0.2 | 0.2 | 0.2 | 0.2 | — | — |
| colorant | 0 | 0.1 | 0 | 0 | — | — |
| % water | 2.3 | 2.3 | 1.2 | 1.2 | ca. 2 | ca. 1 |
| ERH Value: | 37 | 35 | 14.6 | 14.0 | 25 | 19 |

When tested for flexibility, as described above, only Products 3 and 4 were flexible. Thus, only Product 3 and 4 had the desired combination of flexibility and high ERH values.

In addition to being useful in chewing gum products, aspartame stabilized with the cooked hydrogenated starch hydrolysate can also be used in other comestibles or ingested products which might employ a bulk non-nutritive sweetener such as toothpaste, confectionary products including the chewing gum products, including the regular non-bubble gum as well as the bubble gum types, hard candy, liquid filled chewing gum and candy, medicinals such as cough drops, antacids, and breath fresheners; bakery goods such as cookies and others such as salad dressings and puddings.

The aspartame need not be encapsulated or coated in any way when employed in the products of the present invention. It and the other components of such products in which it is used may all be freely dispersed in such products.

The use of cooked hydrogenated starch hydrolysate, as a stabilizer for the L-aspartic acid derivatives in the moisture containing comestible products of the present invention enables the formulator to use about 30 to 50% less of the L-aspartic acid derivative, and still recover the same amounts of L-aspartic acid derivative over the extended storage periods noted above, as when the L-aspartic acid derivative is used in the same comestible product but without the cooked hydrogenated starch hydrolysate stabilizer of the present invention.

The use of the cooked hydrogenated starch hydrolysate stabilizers of the present invention is also useful in stabilizing comestibles such as the chewing gum compositions prepared above which have manufacturing heat histories of at least 115° C. for at least 10–20 minutes and which heat histories may also have a deleterious effect on the stability of the L-aspartic acid sweeteners used wherein.

What is claimed is:

1. In an ingestible sugarless product comprising sweetness imparting amounts of L-aspartic acid derivative sweetening agent, effective amounts of non-nutritive bulk sweetener, and ≧2% moisture, the improvement comprising the inclusion of cooked aqueous hydrogenated starch hydrolysate having a moisture content of 10±6% and in amounts effective to stabilize said L-aspartic acid derivative sweetening agent against decomposition during storage of 30% relative humidity and 100°–105° F. for 40 days, whereby at least 80% of said sweetening agent is retained in said composition in undecomposed form after said storage.

2. A product as in claim 1 in which said cooked moisture content is 10±4%.

3. An ingestible product as in claim 1 which is a chewing gum product having a moisture content of about 2 to 8% and further comprising gum base and non-nutritive bulk sweetener.

4. A product as in claim 1 further comprising about 0 to 12% glycerine.

5. An ingestible product as in claim 4 which is a chewing gum product comprising about 5 to 9% glycerine, gum base and non-nutritive bulk sweetener.

6. A product as in claim 1 comprising about 0.01 to 2% aspartame.

7. A flexible stick chewing gum product made from the composition of claim 6 and further comprising gum base and non-nutritive bulk sweetener.

8. A chewing gum product as in claim 3 having an ERH value of about >25 to 50.

9. A chewing gum product as in claim 8 having an ERH value of about 30 to 40.

10. An ingestible product as in claim 6 which is a chewing gum product comprising gum base and non-nutritive bulk sweetener and having an ERH value of about >25 to 50.

11. A chewing gum product as in claim 10 having an ERH value of about 30 to 40.

12. Sugarless chewing gum comprising gum base, non-nutritive bulk sweetener, and, in weight percent,
(i) about 2 to 8% moisture,
(ii) about 0.01 to 2.0% L-aspartic acid sweetening agent derivative, and
(iii) as a stabilizer for said L-aspartic acid derivative, stabilizingly effective quantities of cooked hydrogenated starch hydrolysate having a moisture content of about $10\pm6\%$,
wherein said composition, upon the storage thereof at 30% relative humidity and 100°–105° F., retains at least 80% of said L-aspartic acid derivative therein in undecomposed form for at least 40 days.

13. Chewing gum as in claim 12 which retains at least 70% of said aspartic acid derivative therein in undecomposed form for at least 50 days.

14. Chewing gum as in claim 12 in which said L-aspartic acid derivative is aspartame.

15. Chewing gum as in claim 12 further comprising 0 to 12% glycerine.

16. A sugarless ingestible composition comprising
(i) at least 2 weight % moisture
(ii) about 0.01 to 2.0 weight % of L-aspartic acid sweetening agent derivative, and
(iii) as a stabilizer for said L-aspartic acid derivative, stabilizingly effective quantities of cooked hydrogenated starch hydrolysate having a moisture content of $10\pm6\%$,
each of said (i) to (iii) components being admixed as such in said composition, and
said composition being adapted, upon the storage thereof at 30% relative humidity and 105° F., to retain at least 70% of said L-aspartic acid derivative therein undecomposed form for at least 55 days.

17. An ingestible composition as in claim 16 which is a chewing gum composition further comprising gum base and non-nutritive bulk sweetener.

18. An ingestible composition as in claim 17 in which said L-aspartic acid sweetening agent derivative is aspartame.

19. An ingestible composition as in claim 18 having a moisture content of about 2 to 8%, an aspartame content of about 0.1 to 0.25, and a cooked hydrogenated starch hydrolysate content of about 10 to 30 weight %.

20. An ingestible composition as in claim 19 further comprising $\geq 0$ to 12 weight % of glycerine.

21. An ingestible composition as in claim 19 having a manufacturing heat history of at least 115° F. for at least 10 to 20 minutes.

22. An ingestible composition as in claim 19 further comprising the following additional components,
15 to 35%: gum base
0 to 5.0%: gum base modifier
20 to 70%: bulk sweetening agent
0.1 to 0.5%: coloring agent
0.5 to 2.5%: flavoring agent.

23. A process for stabilizing the L-aspartic acid sweetening agent derivative of a sugarless ingestible product against decomposition during storage comprising formulating a sugarless ingestible product which comprises, in weight percent, $\geq 2\%$ moisture and 0.01 to 2.0% of said L-aspartic derivative, with about 10 to 30% of cooked hydrogenated starch hydrolysate, and storing said product,
wherein said cooked hydrogenated starch hydrolysate is effective in retaining at last 80% of said L-aspartic acid derivative in undecomposed form during storage at 30% relative humidity and 100°–105° F. for at least 40 days.

24. A process as in claim 23 in which said ingestible product is a chewing gum product comprising gum base and non-nutritive bulk sweetener.

25. A process as in claim 24 in which said L-aspartic acid derivative is aspartame.

* * * * *